US012622947B2

(12) United States Patent
Choi

(10) Patent No.: US 12,622,947 B2
(45) Date of Patent: May 12, 2026

(54) PHARMACEUTICAL COMPOSITION FOR TREATING LEVODOPA-INDUCED DYSKINESIA OR FOR SUPPRESSING PROGRESSION THEREOF

(71) Applicant: PEPTRON, INC., Daejeon (KR)

(72) Inventor: Ho Il Choi, Daejeon (KR)

(73) Assignee: PEPTRON, INC., Daejeon (KR)

( * ) Notice: Subject to any disclaimer, the term of this patent is extended or adjusted under 35 U.S.C. 154(b) by 580 days.

(21) Appl. No.: 17/630,799

(22) PCT Filed: Jul. 29, 2020

(86) PCT No.: PCT/KR2020/010023
§ 371 (c)(1),
(2) Date: Jan. 27, 2022

(87) PCT Pub. No.: WO2021/020885
PCT Pub. Date: Feb. 4, 2021

(65) Prior Publication Data
US 2022/0273769 A1 Sep. 1, 2022

Related U.S. Application Data

(60) Provisional application No. 62/879,574, filed on Jul. 29, 2019.

(30) Foreign Application Priority Data

Jul. 29, 2020 (KR) ........................ 10-2020-0094783

(51) Int. Cl.
| | |
|---|---|
| *A61K 38/26* | (2006.01) |
| *A61K 9/20* | (2006.01) |
| *A61K 9/28* | (2006.01) |
| *A61P 25/16* | (2006.01) |

(52) U.S. Cl.
CPC .............. *A61K 38/26* (2013.01); *A61K 9/204* (2013.01); *A61K 9/282* (2013.01); *A61P 25/16* (2018.01)

(58) Field of Classification Search
CPC ........ A61K 38/26; A61K 9/204; A61K 9/282; A61K 9/0019; A61K 9/10; A61K 9/1647; A61K 9/19; A61K 47/26; A61K 47/38; A61K 31/198; A61K 38/22; A61P 25/16; A61P 25/14
See application file for complete search history.

(56) References Cited

U.S. PATENT DOCUMENTS

| | | | |
|---|---|---|---|
| 2004/0087596 A1* | 5/2004 | Schneider ............ | A61K 31/198 514/567 |
| 2022/0041684 A1* | 2/2022 | Patterson ........... | A61K 40/4211 |

FOREIGN PATENT DOCUMENTS

| | | |
|---|---|---|
| EP | 2 193 794 A1 | 6/2010 |
| KR | 10-100805208 B1 | 2/2008 |
| KR | 10-2016-0066850 A | 6/2016 |
| WO | WO 2008/117927 A1 | 10/2008 |
| WO | WO 2012/010896 A1 | 1/2012 |
| WO | WO 2017/112889 A1 | 6/2017 |
| WO | WO 2018/075901 A1 | 4/2018 |
| WO | WO-2018204764 A1 * | 11/2018 .............. G16B 25/10 |

OTHER PUBLICATIONS

Aviles-Olmos et al. Exenatide and the treatment of patients with Parkinson's disease, The Journal of Clinical Investigation, vol. 123 No. 6 Jun. 2013, pp. 2730-2736. (Year: 2013).*
Bader et al. Pharmacokinetics and efficacy of PT302, a sustained-release Exenatide formulation, in a murine model of mild traumatic brain injury. Neurobiol Dis, Apr. 2019, vol. 124, pp. 439-453. (Year: 2019).*
Harkavyi_et_al_J_of_Neuroinflammation_2008 (Year: 2008).*
European Search Report For EP20846757.1 issued on Jul. 12, 2023 from European patent office in a counterpart European patent application.
Yu Seong-Jin et al., "PT320, Sustained-Release Exendin-4, Mitigates L-DOPA-Induced Dyskinesia in a Rat 6-ydroxydopamine Model of Parkinson's Disease", Frontiers in Neuroscience, vol. 14, pp. 1-9, 2020.
Search Report For 11202200765T issued on May 1, 2023 from Intellectual Property Office of Singapore (all the cited references are listed in this IDS.).
Office action issued on Dec. 8, 2023 from China Patent Office in a counterpart China Patent Application No. 202080054823.6 (all the cited references are listed in this IDS.) (English translation is also submitted herewith.).
International Search Report for PCT/KR2020/010023 mailed on Nov. 6, 2020.
Abuirmeileh, Amjad et al. "Exendin-4 treatment enhances L-DOPA evoked release of striatal dopamine and decreases dyskinetic movements in the 6-hydoxydopamine lesioned rat : Exendin and L-DOPA dyskinesias ", Journal of Pharmacy and Pharmacology. 2012, vol. 64, pp. 637-643. See abstract, pp. 638-638 and 642 and Fig. 1-4.
Elabi, Osama Falah. "The effect of L-dopa and neuroprotective agents on cell replacement therapy for Parkinson's disease.", Ph.D. thesis, Cardiff University, 2017, See p. 123.
Stanley Fahn, "Description of Parkinson's Disease as a Clinical Syndrome", N Y Acad Sci. Jun. 2003;991:1-14. doi: 10.1111/j.1749-6632.2003.tb07458.x.
C. Warren Olanow et al. "An algorithm (decision tree) for the management of Parkinson's disease (2001): Treatment Guidelines", Neurology 56, Suppl.5, 2001.

(Continued)

*Primary Examiner* — Catherine S Hibbert
(74) *Attorney, Agent, or Firm* — Travis Young; Bret E. Field; Bozicevic, Field & Francis LLP

(57) ABSTRACT

A GLP-1 receptor agonist has effects of reducing serious side effects due to long-term use of levodopa when administered in combination with levodopa, and also effects of alleviating or improving abnormal involuntary movements (AIMs) caused by levodopa. A method for prevention or treatment of levodopa-induced dyskinesia according to an embodiment of the present disclosure includes administering a glucagon-like peptide-1 (GLP-1) receptor agonist to a patient.

10 Claims, 4 Drawing Sheets

(56)          References Cited

OTHER PUBLICATIONS

Joseph Jankovic, "Motor Fluctuations and Dyskinesias in Parkinson's Disease: Clinical Manifestations", Movement Disorders, vol. 20, Suppl. 11, 2005, pp. S11-S16.

John G. Nutt, "Levodopa-induced dyskinesia: Review, observations, and speculations", Neurology, 1990, vol. 40, pp. 340-345.

Niall Quinn, "Drug treatment of Parkinson's disease", British Medical Journal, 1995, vol. 310, pp. 575-579, London.

C. Warren Olanow et al. "Levodopa in the Treatment of Parkinson's Disease: Current Controversies", Movement Disorders vol. 19, No. 9, 2004, pp. 997-1005.

Joshua D. Berke et al. "A Complex Program of Striatal Gene Expression Induced by Dopaminergic Stimulation", The Journal of Neuroscience, 1998, vol. 18(14), pp. 5301-5310.

Malin Andersson et al. " cAMP Response Element-Binding Protein Is Required for Dopamine-Dependent Gene Expression in the Intact But Not the Dopamine-Denervated Striatum", The Journal of Neuroscience, 2001, vol. 21(24), pp. 9930-9943.

Malin Andersson et al. "Striatal fosB Expression Is Causally Linked with L-DOPA-Induced Abnormal Involuntary Movements and the Associated Upregulation of Striatal Prodynorphin mRNA in a Rat Model of Parkinson's Disease", Neurobiology of Disease 6, 1999, pp. 461-474.

Nancy Pavon et al. " ERK Phosphorylation and FosB Expression Are Associated with L-DOPA-Induced Dyskinesia in Hemiparkinsonian Mice", Biological Psychiatry, vol. 59, 2006, pp. 64-74.

Jenny E. Westin et al. "Spatiotemporal Pattern of Striatal ERK1/2 Phosphorylation in a Rat Model of L-DOPA-Induced Dyskinesia and the Role of Dopamine D1 Receptors", Biological Psychiatry, vol. 62(7), 2007, pp. 800-810.

S.-L.C. Jin et al. " Distribution of Glucagonlike Peptide I(GLP-I), Glucagon, and Glicentin in the Rat Brain: An Immunocytochemical Study", The Journal of Comparative Neurology, vol. 271, 1988, pp. 519-532.

Paul J. Shughrue et al. "Glucagon-Like Peptide-I Receptor (GLPI-R) mRNA in the Rat Hypothalamus", Endocrinology, vol. 137, No. 11, 1996, pp. 5159-5162.

Guanghong Jia et al. "Glucagon-Like Peptide 1 Receptor Activation and Platelet Function: Beyond Glycemic Control", Diabetes, vol. 65, 2016.

Yang Wei et al. "Tissue-specific expression of the human receptor forglucagon-like peptide-I: brain, heart and pancreatic forms have the same deduced amino acid sequences", FEBS Letters 358, 1995, pp. 219-224.

Fumitoshi Satoh et al. "Characterization of Human and Rat Glucagon-Like Peptide-1 Receptors in the Neurointermediate Lobe: Lack of Coupling to Either Stimulation or Inhibition of Adenylyl Cyclase", Endocrinology, vol. 141, No. 4, 2000, pp. 1301-1309.

Robert V. Campos et al. "Divergent Tissue-Specific and Developmental Expression of Receptors for Glucagon and Glucagon-Like Peptide-1 in the Mouse", Endocrinology, vol. 134, No. 5, 1994, pp. 2156-2164.

José C. Calvo et al. "Structural Characterization by Affinity Cross-Linking of Glucagon-Like Peptide-1 (7-36) Amide Receptor in Rat Brain", Journal of Neurochemistry, vol. 64, No. 1, 1995, pp. 299-306.

Rudiger Goke et al. "Distribution of GLP-1 Binding Sites in the Rat Brain: Evidence that Exendin-4 is a Ligand of Brain GLP-1 Binding Sites", European Journal of Neuroscience, vol. 7, 1995, pp. 2294-2300.

Zengbing Lu et al. "Differential hypoglycaemic, anorectic, autonomic and emetic effects of the glucagon-like peptide receptor agonist, exendin-4, in the conscious telemetered ferret", Journal of Translational Medicine, 12, Article No. 327, 2014.

Matthew J During et al. "Glucagon-like peptide-1 receptor is involved in learning and neuroprotection", Nature Medicine 9, 2003, pp. 1173-1179.

Byung-Joon Kim et al. "Transferrin Fusion Technology: A Novel Approach to Prolonging Biological Half-Life of Insulinotropic Peptides", The Journal of Pharmacology and Experimental Therapeutics, vol. 334, No. 3, 2010, pp. 682-692.

Bronwen Martin et al. "Euglycemic Agent-mediated Hypothalamic Transcriptomic Manipulation in the N171-82Q Model of Huntington Disease Is Related to Their Physiological Efficacy", The Journal of Biological Chemistry, vol. 287, No. 38, 2012, pp. 31766-31782.

AJ Kastin et al. "Entry of exendin-4 into brain is rapid but may be limited at high doses", International Journal of Obesity, 27, 2003, pp. 313-318.

WeiZhen Liu et al. "Neuroprotective effects of lixisenatide and liraglutide in the MPTP mouse model of Parkinson's disease", Jun. 2015 Neuroscience 303 DOI:10.1016/j.neuroscience.2015.06.054.

Office action issued on Jul. 26, 2022 from Korean Patent Office in a counterpart Korean Patent Application No. 10-2020-0094783 (all the cited references are listed in this IDS.).

Ghada A. Badawi et al., "Sitagliptin and Liraglutide Modulate L-dopa Effect and Attenuate Dyskinetic Movements in Rotenone-Lesioned Rats", Neurotoxicity Research, 2019, vol. 35, pp. 635-653.

Communication pursuant to Article 94(3) EPC of EP 20 846 757.1 issued on Mar. 31, 2025 from European patent office in a counterpart European patent application.

Shivakalyani Adepu et al., "Controlled Drug Delivery Systems: Current Status and Future Directions", Molecules, vol. 26(19), 5905, 2021.

Badawi et al., Sitagliptin and Liraglutide Modulate L-dopa Effect and Attenuate Dyskinetic Movements in Rotenone-Lesioned Rats, Neurotox Res, 35(3):635-653 (Apr. 2019).

* cited by examiner

FIG. 4

PHARMACEUTICAL COMPOSITION FOR TREATING LEVODOPA-INDUCED DYSKINESIA OR FOR SUPPRESSING PROGRESSION THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2020/010023 with an International Filing Date of Jul. 29, 2020, which claims the benefit of U.S. Application No. 62/879,574 filed on Jul. 29, 2019 and Korean Patent Application No. 10-2020-0094783 filed on Jul. 29, 2020 at the Korean Intellectual Property Office, the disclosures of which are incorporated by reference herein in their entirety.

BACKGROUND

1. Technical Field

The present invention relates to a pharmaceutical composition for treating or inhibiting progression of levodopa-induced dyskinesia, and a method for treating or inhibiting progression of levodopa-induced dyskinesia using the pharmaceutical composition.

2. Background Art

Parkinson's disease (PD) is a neurological disorder caused by degeneration of the dopaminergic neuron of the striatum-black substance ("nigrostriatal") of the cerebral basal ganglia, and a disease involving symptoms of behavior dysfunctions such as slow behavior, stiffness of the body, tremor and unstable posture (Fahn, 2003). As a primary drug therapy for Parkinson's disease, L-3,4-dihydroxyphenylalanine (L-DOPA) therapy as a dopamine agonist or dopamine precursor is mainly selected and implemented (Olanow et al., 2001). However, long-term L-DOPA therapy in animal models of Parkinson's disease has caused neurotoxicity due to formation of reactive oxygen species (ROS) and changes in downstream gene/protein expression, and long-term administration of L-DOPA in Parkinson's disease patients has not only decreased drug efficacy but also caused dyskinesia, motor fluctuation and other complications (Jankovic, 2005).

Dyskinesia is a side effect of abnormal movement caused by confusion due to reflux waves in motor muscles, and it has been reported that 40% of patients who have L-DOPA treatment for 4 to 5 years and 90% of patients who have the same treatment for 9 to 15 years exhibited the above symptom (Nutt, 1990; Quinn, 1995). This dyskinesia is called peak-dose dyskinesia because it responds and is exhibited when the concentration of L-DOPA in the brain is highest (Olanow et al., 2004).

The mechanism of levodopa-induced dyskinesia (LID) is not known exactly, but results of increased sensitivity to dopamine D1 and D2 receptors in striatum due to dopamine reduction are suggested as one cause. This increase in dopamine D1 and D2 receptor sensitivity causes a rapid change in dopamine concentration. Long-term administration of dopamine D1 and D2 agonists causes expression of dyskinesia in the animal model of Parkinson's disease (Berke et al., 1998).

Further, levodopa-induced dyskinesia is related to the expression of genes and proteins in the striatum in which the dopamine nerve is destroyed. In particular, several studies have reported that ΔFosB protein expression and phosphorylation of extracellular signal-regulated kinase 1/2 (ERK1/2) are highly correlated (Andersson et al., 2001; Pavon N. et al., 2006).

There is a study reporting that long-term administration of L-DOPA to a Parkinson's disease animal model using 6-hydroxydopamine (6-OHDA) results in dyskinesia along with ΔFosB protein expression (Andersson et al., 1999). Recently, studies have reported that phosphorylation of ERK1/2 is associated with an increase in the expression of ΔFosB protein due to dyskinesia (Pavon N. et al., 2006). Further, there is a study reporting that administration of a physiological saline solution in 6-OHDA-induced Parkinson's disease animal models did not affect ERK1/2 phosphorylation, whereby ERK1/2 phosphorylation by L-DOPA administration was related to the expression of abnormal involuntary movements (AIMs), which indicates a degree of dyskinesia. (Westin et al., 2007).

Meanwhile, a GLP-1 receptor is present in both the rodent brain (Jin et al., 1988; Shughrue et al., 1996; Jia et al., 2016) and the human brain (Wei, Mojsov 1995; Satoh et al., 2000). According to the chemical structure, it generally appears that the distribution is mainly confined to the area postrema, that is, the hypothalamus, thalamus, brainstem, lateral septum and subformical organ, and all circumventricular areas where most of peptide receptors are present.

Further, even with a lower density, specific binding sites for GLP-1 were detected throughout the caudate, putamen, cerebral cortex and cerebellum (Campos et al., 1994; Calvo et al., 1995; Goke et al., 1995). In prior literatures, it was demonstrated that GLP-1 receptors are expressed in the amygdala, cerebellum, frontal cortex, hippocampus, hypothalamus, midbrain, medulla, pons, striatum, thalamus and temporal cortex of the ferrets (*Mustela putorius furo*) (Lu et al., 2014). The expression level of the GLP-1 receptor in the brain is not affected by aging.

Further, GLP-1 has been shown to be related to cognition and behavior (During et al., 2003). A number of studies have suggested GLP-1 receptor agonists as a new therapeutic agent for degenerative brain diseases including Parkinson's disease, Alzheimer's disease, Huntington's disease, traumatic brain injury, stroke and peripheral neurosis. However, a practical obstacle in the treatment of the degenerative brain diseases as described above is the delivery of drugs to the central nervous system across the blood-cerebral barrier (BBB).

For example, GLP-1 has a short half-life of 1 to 2 minutes, and a GLP-1-transferrin fusion protein (GLP-1-Tf) created to increase the half-life of GLP-1 by about 2 days when implying resistance to inactivation of GLP-1 cannot cross over the BBB (Kim et al., 2010; Martin et al., 2012).

Exendin-4 has been shown to improve rotarod performance compared to GLP-1-Tf (Martin et al., 2012), and it is known to enter the brain from blood although its entry speed is limited (Kastin A J et al., 2003). Further, it was found that exendin-4 is not effective in providing neuro-protection in an MPTP mouse model for Parkinson's disease, even when extendin-4 is given daily for 7 days after treatment (Liu et al., 2015).

Therefore, studies are further needed to treat, inhibit or improve involuntary dyskinesia caused by long-term L-DOPA therapy in the treatment of Parkinson's disease.

SUMMARY

An object of the present invention is to provide a pharmaceutical composition for treatment or prevention of levodopa-induced dyskinesia.

Another object of the present invention is to provide a method for treating or preventing levodopa-induced dyskinesia.

To achieve the above objects, the present invention provides a pharmaceutical composition for treating or preventing levodopa-induced dyskinesia, which includes a GLP-1 receptor agonist or a controlled-release formulation thereof.

The glucagon-like peptide-1 receptor agonist (GLP-1 receptor agonist) of the present invention may include a GLP-1 analogue, and more specifically, exendin-4, exenatide, liraglutide, semaglutide, lixisenatide, dulaglutide, albiglutide, efpeglenatide, or a combination thereof, but it is not limited thereto.

The controlled-release formulation of the present invention may include: a core containing a GLP-1 receptor agonist and a biodegradable polymer; and a coating layer for the core.

The biodegradable polymer of the present invention may include a polymer selected from the group consisting of: polylactide, polyglycolide, poly(lactide-co-glycolide) as a copolymer of lactide and glycolide, polyorthoester, polyanhydride, polyhydroxybutyric acid, polycaprolactone and polyalkyl carbonate; a copolymer or mixture of two or more of the above polymers; a copolymer of the above polymer and polyethylene glycol; and a polymer-sugar complex in which the above polymer or copolymer is combined with sugar.

In the present invention, treatment is a concept including improvement in symptoms of levodopa-induced dyskinesia or no further worsening of symptoms.

In the present invention, prevention is a concept including prevention or delayed onset of levodopa-induced dyskinesia despite administration of levodopa.

The pharmaceutical composition of the present invention may have effects of improving abnormal involuntary movements (AIMs), and the pharmaceutical composition of the present invention may also have effects of reducing the side effects due to long-term administration of levodopa when administered in combination with levodopa.

The present invention provides a method for treatment of levodopa-induced dyskinesia, which includes administering a therapeutically effective amount of a GLP-1 receptor agonist or a controlled-release formulation thereof to a patient having levodopa-induced dyskinesia.

The present invention provides a method for prevention of levodopa-induced dyskinesia, which includes administering a prophylactically effective amount of a GLP-1 receptor agonist or a controlled-release formulation thereof to a Parkinson's disease patient who does not involve development of levodopa-induced dyskinesia.

In the treatment or prevention method of the present invention, both patients with levodopa-induced dyskinesia and Parkinson's patients who do not involve development of levodopa-induced dyskinesia may be patients receiving levodopa administration.

In the treatment or prevention method of the present invention, the GLP-1 receptor agonist or the controlled-release formulation thereof may be administered simultaneously with levodopa or after administration of levodopa.

The therapeutically effective amount of the active ingredient in the treatment method of the present invention may range from 0.01 μg/kg/day to 100 μg/kg/day.

In the prevention method of the present invention, a prophylactically effective amount of the active ingredient may range from 0.01 μg/kg/day to 100 μg/kg/day.

In the treatment or prevention method of the present invention, the GLP-1 receptor agonist may include a GLP-1 analogue, and more specifically, exendin-4, exenatide, liraglutide, semaglutide, lixisenatide, dulaglutide, albiglutide, efpeglenatide, or a combination thereof, but it is not limited thereto.

In the treatment or prevention method of the present invention, the controlled-release formulation may include: a core containing the GLP-1 receptor agonist and a biodegradable polymer; and a coating layer for the core.

In the treatment or prevention method of the present invention, the biodegradable polymer may be at least one selected from the group consisting of: a polymer selected from the group consisting polylactide polyglycolide, poly (lactide-co-glycolide) as a copolymer of lactide and glycolide, polyorthoester, polyahydride, polyhydroxybutyric acid, polycaprolactone and polyalkyl carbonate; a copolymer or mixture of two or more of the above polymers; a copolymer of the above polymer and polyethyleneglycol; and a polymer-sugar complex formed of the above polymer or copolymer combined with sugar.

The present invention provides a use of a GLP-1 receptor agonist or a controlled-release formulation thereof in manufacturing a therapeutic agent for levodopa-induced dyskinesia.

The present invention relates to a pharmaceutical composition for treatment or prevention of levodopa-induced dyskinesia. The GLP-1 receptor agonist or the controlled-release formulation thereof according to the present invention has effects of reducing serious side effects due to long-term use of levodopa when administered in combination with levodopa, and also effects of alleviating or improving abnormal involuntary movements (AIMs) caused by levodopa.

BRIEF DESCRIPTION OF THE DRAWINGS

FIG. 4 is a graph confirming the effect of reducing AIMs in a time-dependent manner by treatment with a controlled-release formulation (PT320) of the GLP-1 receptor agonist according to an example of the present invention in LID-induced rats.

DETAILED DESCRIPTION

Figure 1:
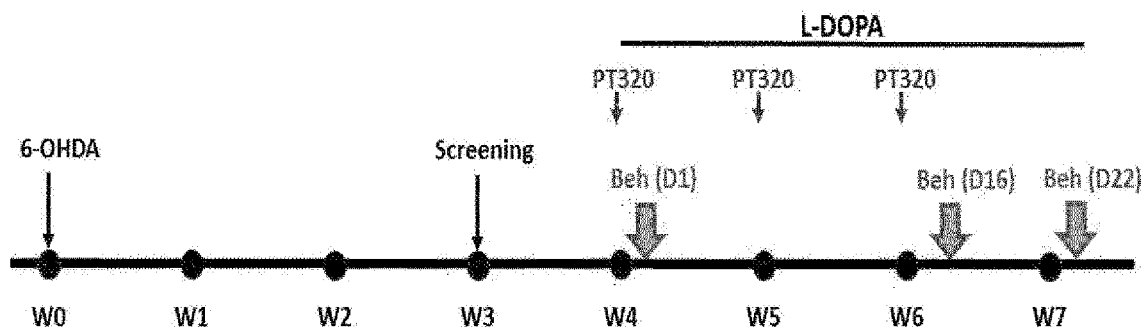
FIG. 1 is a diagram showing a drug treatment schedule for a controlled-release formulation (PT320) of a GLP-1 receptor agonist according to an example of the present invention over time.

The present invention provides a pharmaceutical composition for treatment or prevention of levodopa-induced dyskinesia, which includes a GLP-1 receptor agonist or a controlled-release formulation thereof.

The glucagon-like peptide-1 receptor agonist (GLP-1 receptor agonist) may include a GLP-1 analogue, and more specifically, exendin-4, exenatide, liraglutide, semaglutide, lixisenatide, dulaglutide, albiglutide, efpeglenatide, or a combination thereof, but it is not limited thereto.

The controlled-release formulation means a formulation having excellent bioavailability by effectively controlling an initial release amount of the GLP-1 receptor agonist to enable sustained and sufficient release of the drug.

The levodopa-induced dyskinesia is involuntary dyskinesia induced by levodopa, and shows a status of choreoathetosis or dystonia occurring in a limb or trunk. Such symptoms as described above are common in patients who have taken levodopa for a long period of time and may mean side effects causing serious obstacles in daily life, if severe.

The term "treatment" refers to any action including improving or no further worsening of symptoms of levodopa-induced dyskinesia.

The term "prevention" refers to any action including preventing or delaying the onset of levodopa-induced dyskinesia despite administration of levodopa.

The term "administration" means introducing a predetermined substance to an individual in an appropriate way, and "individual" means all animals including rats, mice, livestock, etc., as well as humans who have or may involve development of levodopa-induced dyskinesia by administration of levodopa. As a specific example, it may be a mammal including a human.

The pharmaceutical composition of the present invention may be in the form of capsules, tablets, granules, injections, ointments, powders or beverages, and may be formulated and used in oral dosage forms such as powders, granules, capsules, tablets, aqueous suspensions, and the like, external preparations, suppositories and injections.

The formulation of the pharmaceutical composition of the present invention may be prepared in various ways by mixing the composition with a pharmaceutically acceptable carrier. For example, when administered orally, it may be prepared in the forms of tablets, troches, capsules, elixir, suspension, syrup, wafers, etc. Further, in the case of an injection, it may be prepared in a unit dosage ampoule or a multiple dosage form. In addition, the formulation of the pharmaceutical composition of the present invention may be prepared as a solution, suspension, tablet, capsule, sustained-release formulation, or the like.

The pharmaceutical composition of the present invention may contain an active ingredient alone, or may further include one or more pharmaceutically acceptable carriers, excipients, or diluents.

Pharmaceutically acceptable carriers for oral administration may be binders, lubricants, disintegrants, excipients, solubilizers, dispersants, stabilizers, suspending agents, coloring agents, flavoring agents, etc. In the case of an injection formulation, a buffering agent, a preservative, a painless agent, a solubilizing agent, an isotonic agent, a stabilizer, etc. may be mixed and used. Further, for topical administration, a base agent, an excipient, a lubricant, a preservative, and the like may be used.

Carriers, excipients and diluents for formulation may include, for example, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, mineral oil, filler, anti-coagulants, lubricants, wetting agents, fragrance, emulsifiers or preservatives.

Administration routes of the pharmaceutical composition of the present invention may be oral, intravenous, intramuscular, intraarterial, intramedullary, intrathecal, intracardiac, transdermal, subcutaneous, intraperitoneal, intranasal, intestinal, topical, sublingual or rectal, but it is not limited thereto.

The pharmaceutical composition of the present invention may be administered orally or parenterally, and is preferably administered by a parenteral route. For parenteral administration, external dosage forms for skin, or intraperitoneal injection, rectal injection, subcutaneous injection, intravenous injection, intramuscular injection or intrathoracic injection method may be selected.

The dosage of the pharmaceutical composition of the present invention may vary depending on the age, condition and weight of the patient, severity of disease, drug forms, the route and duration of administration, but may be appropriately selected by those skilled in the art. For example, the pharmaceutical composition of the present invention may be administered at 0.0001 to 1000 mg/kg or 0.001 to 500 mg/kg per day. Further, on the basis of the amount of active ingredient, it may be administered in 0.01 to 100 μg/kg/day, preferably 0.1 to 10 μg/kg/day.

Administration of the pharmaceutical composition of the present invention may be administered once a day, or may be divided several times. The above dosage does not limit the scope of the present invention in any way.

The controlled-release formulation of the present invention may mean a pharmaceutical composition which includes: a core containing a GLP-1 receptor agonist and a biodegradable polymer; and a coating layer for the core.

The biodegradable polymer is a generic term for a polymer that is slowly decomposed and discharged when administered into the body and is harmless to the human body. The biodegradable polymer may include: at least one polymer selected from the group consisting of polylactide (PLA), polyglycolide (PGA), poly(lactide-co-glycolide) (PLGA) as a copolymer of lactide and glycolide, polyorthoester, polyanhydride, polyhydroxybutyric acid, polycaprolactone and polyalkylcarbonate; and a copolymer of the above polymer and polyethylene glycol (PEG), wherein the at least one polymer may be a copolymer or a simple mixture form.

Among the biodegradable polymers, in particular, polyester series such as PLA, PGA and PLGA are hydrolyzed in the body and metabolized into lactic acid and glycolic acid, which are harmless to the human body, whereby these are recognized to have biocompatibility and stability. Further, a biodegradation rate thereof may also be variously adjustable from 1-2 weeks to 1-2 years depending on a molecular weight of the polymer, a relative ratio of two monomers, hydrophilicity, etc. In fact, these polymers have been approved and commercialized in dozens of countries including the US FDA, therefore, can be preferably used in the present invention. Specifically, the polyester-based polymers such as PLGA, PLA, etc. are more preferably used in the present invention.

In another aspect, the biodegradable polymer may be one polymer or two or more copolymers selected from the group consisting of polylactide (PLA), polyglycolide (PGA), poly (lactide-co-glycolide) (PLGA) as a copolymer of lactide and glycolide, polyorthoester, polyanhydride, polyhydroxybutyric acid, polycaprolactone and polyalkylcarbonate; and a complex of one or more polymers selected from the group consisting of copolymers including the above polymers and polyethyleneglycol (PEG) and sugar (hereinafter, referred to as "polymer-sugar complex").

The polymer-sugar complex in the present invention refers to a form in which the above-described polymer is substituted at a hydroxy group position of the sugar. The sugar contains one or more, preferably 1 to 8 saccharide units, and each saccharide unit is a monosaccharide or polysaccharide having 3 to 6 hydroxy groups or is a sugar alcohol in a linear chain structure, which has a molecular weight of 20,000 or less and 3 to 6 hydroxy groups. The sugar alcohol may include mannitol, pentaerythritol, sorbitol, ribitol, xylitol and the like. The polymer is bound to three or more of the hydroxy groups present in the sugar.

Further, the biodegradable polymer can be used without limitation of viscosity. However, if a viscosity of the polymer is too low, the drug cannot be effectively protected while increasing the initial release amount of the drug. On the other hand, if the viscosity is too high, the overall release amount of the drug is low and the bioavailability is reduced. Therefore, the intrinsic viscosity is preferably 0.1 to 0.5 dL/g.

The coating material is used for the purpose of preventing excessive initial release of the drug and increasing bioavailability. In the controlled-release formulation according to the present invention, the coating material may be present in the form of coating layer formed on an outside.

The coating material may be at least one selected from the group consisting of basic amino acids, polypeptides and organic nitrogen compounds. The basic amino acids may include arginine, lysine, histidine, and derivatives thereof. Further, the polypeptide may be 2 to 10 amino acids, preferably 2 to 5 amino acids including at least one selected from the group consisting of arginine, lysine and histidine. Among the total number of amino acids in the polypeptide, the number of basic amino acids is greater than the number of acidic amino acids, thereby appearing basicity.

The controlled-release formulation of the present invention may be prepared according to various methods, and sustained-release microspheres of the present invention may also be prepared by suspending microspheres in an aqueous coating material solution to coat the surface of the microspheres with the coating material during or after preparation of the microspheres. The method of manufacturing microspheres according to the present invention may adopt a double emulsion evaporation method (W/O/W method), a single emulsion evaporation method (O/W method), a phase separation method, a spray-drying method and the like.

In more detail, the method for production of exenatide-containing sustained-release microspheres according to the present invention may include: mixing exenatide and a biodegradable polymer to prepare a W/O-type emulsion or a homogeneous mixture; and applying the emulsion or homogeneous mixture to an aqueous solution of a coating material to emulsify the same, thereby forming a coating layer. More specifically, in the case of using the double emulsification evaporation method, the production method of the present invention may include: forming a primary emulsion (W/O) by emulsifying an aqueous exenatide solution and an organic solvent in which a biodegradable polymer is dissolved; suspending the emulsion in an aqueous coating material solution to form a W/O/W emulsion; heating the same to remove the organic solvent and curing the residue; and recovering the cured microspheres, washing with water and lyophilizing the same. The organic solvent may be any organic solvent capable of dissolving the biodegradable polymer and forming an emulsion when mixed with an aqueous solution. For example, one or more species selected from the group consisting of acetic acid, chloroform, ethyl acetate, methylene chloride and methyl ethyl ketone may be included, In this case, the coating material is included in the secondary aqueous phase (the external aqueous phase of the W/O/W emulsion) and, when the organic solvent is removed and dried, a coating layer is formed on the outside of exenatide and the biodegradable polymer. Further, when using the single emulsification evaporation method, the production method of the present invention may include: a process of dissolving a biodegradable polymer and exenatide in an organic solvent to prepare a homogeneous mixture, preparing an emulsion by adding an aqueous coating material solution to the homogeneous mixture, heating to remove the organic solvent and curing the residue; and process of recovering the cured microspheres, washing with water and lyophilizing the same.

The organic solvent may uniformly blend the biodegradable polymer and exenatide, and any organic solvent able to be mixed with an aqueous solution to form an emulsion may be used. For example, a mixture including at least one solvent selected from the group consisting of alcohols having 1 to 5 carbon atoms, glacial acetic acid, formic, acid, dimethyl sulfoxide and n-methyl pyrrolidone, and at least one solvent selected from the group consisting of chloroform, ethyl acetate, methylethyl ketone and methylene chloride, and more preferably, a mixed solvent of methanol and methylene chloride is used. At this time, by emulsifying the homogeneous mixture of the biodegradable polymer and exenatide and adding a coating material to an aqueous solution to remove the organic solvent, a coating layer may be formed on the surface of the finally obtained microspheres.

Further, in the case of using the single emulsification evaporation method, the production method of the present invention may include: dissolving a biodegradable polymer and exenatide in an organic solvent to prepare a homogeneous mixture; preparing an emulsion by adding aqueous coating material solution to the homogeneous mixture, followed by heating to remove the organic solvent and curing the residue; and recovering the cured microspheres, washing with water and lyophilizing the same.

The solvent may uniformly blend the biodegradable polymer and exenatide, and any organic solvent able to be mixed with an aqueous solution to form an emulsion may be used. For example, a mixture including at least one solvent selected from the group consisting of alcohols having 1 to 5 carbon atoms, glacial acetic acid, formic acid, dimethyl sulfoxide and n-methyl pyrrolidone, and at least one solvent selected from the group consisting of chloroform, ethyl acetate, methylethyl ketone and methylene chloride, may be used. In this case, by emulsifying the homogeneous mixture of the biodegradable polymer and exenatide and adding a coating material to an aqueous solution in order to remove the organic solvent, a coating layer may be formed on the surface of the finally obtained microspheres. In another aspect, the method for manufacturing exenatide-containing sustained-release microspheres of the present invention may include: mixing exenatide and a biodegradable polymer to prepare an emulsion or a homogeneous mixture; powdering the emulsion or homogeneous mixture obtained above to prepare primary microspheres; and suspending the obtained primary microspheres in an aqueous coating material solution to form a coating layer. The powdering method is not limited, and all powdering methods commonly used in the related art may be used, for example, a phase separation method or a spray-drying method may be used.

More specifically, when the phase separation method is used for powdering, the manufacturing method of the present invention may include: mixing an exenatide solution and an organic solvent, in which a polymer is dissolved, to prepare an emulsion, or mixing exenatide and a polymer with a mixed solvent to prepare a homogeneous mixture solution; adding oil such as silicone oil to form primary microspheres; adding a non-solvent of a biodegradable polymer, for example, a mixed solvent of an alcohol having 1 to 5 carbon atoms and an alkane having 1 to 12 carbon atoms, preferably, a mixed solvent of ethanol and heptane to the primary microspheres in order to remove the organic solvent from the microspheres and cure the primary microspheres; suspending the obtained microspheres in an aqueous coating material solution to form a coating layer; and recovering the microspheres on which the coating layer is formed, washing and lyophilizing the same.

The organic solvent may be at least one selected from the group consisting of chloroform, ethyl acetate, methylene chloride, and methylethylketone, and preferably methylene chloride. Further, the mixed solvent may be a mixed solvent including one or more solvents selected from the group consisting of alcohols having 1 to 5 carbon atoms, glacial acetic acid, formic acid, dimethyl self oxide and n-methyl pyrrolidone, and one or more solvents selected from the group consisting of chloroform, ethyl acetate, methylethylketone and methylene chloride, preferably a mixed solvent of methanol and methylene chloride.

Further, in the case of using the spray-drying method, the manufacturing method of the present invention may include: mixing an aqueous solution of exenatide and an organic solvent, in which a polymer is dissolved, to prepare an emulsion or mixing exenatide and a polymer with a single solvent or a mixed solvent to prepare a uniform solution; spray-drying the solution or emulsion to form primary microspheres; suspending the obtained primary microspheres in an aqueous coating material solution to form a coating layer; and washing the obtained coated microspheres with water and lyophilizing the same.

The organic solvent used herein may be at least one selected from the group consisting of chloroform, ethyl acetate, methylene chloride and methylethylketone, and preferably methylene chloride. Further, the single solvent may be one or more selected from the group consisting of glacial acetic acid or formic acid, while the mixed solvent may be a mixed solvent including one or more solvents selected from the group consisting of alcohols having 1 to 5 carbon atoms, glacial acetic acid, formic acid, dimethyl sulfoxide and n-methyl pyrrolidone, and one or more solvents selected from the group consisting of chloroform, ethyl acetate, methylethylketone and methylene chloride.

The manufacturing method of the present invention may further include adding a protective colloidal material according to a conventional method and, in specific embodiments, the protective colloidal material may be added when applying the coating material to the microspheres. The coating material dissolved in an aqueous phase or the aqueous coating material solution used in the production method according to the present invention may be used in a concentration of 0.01 M to 1 M, and more preferably 0.1 M to 0.5 M. If the concentration of the aqueous coating material solution is lower than the above range, the coating material cannot be sufficiently applied to the surface of the microspheres. Further, if it is higher than the above range, a supersaturated solution of the coating material is resulted. Even using the supersaturated solution, it does not improve the initial release suppression effect more than that in the saturated solution. Therefore, the coating material concentration used for producing the microspheres of the present invention is preferably within the above range.

Hereinafter, preferred embodiments of the present invention will be described in detail to concretely describe the present invention by way of the following examples.

Example 1. Preparation of SR-exenatide (PT320)

The controlled-release formulation (PT320) containing exenatide of the present invention is possibly produced by a double emulsification method (W/O/W method), a single emulsification method (O/W method), a phase separation method, a spray-drying method, and the like (see Korean Patent Registration No. 10-0805208 and International Patent Publication No. PCT/US2017/057606, etc.), In the present example, an exenatide-containing controlled-release formulation (PT320) was prepared by a spray-drying method.

4.850 g of biodegradable polymer RG502H and 0.150 g of exenatide acetate (Polypeptide Laboratory, USA) were uniformly dissolved in 97 ml of glacial acetic acid. The prepared solution was supplied to a spray dryer (SODEVA, France) equipped with an ultrasonic nozzle (Sono-tek, 120 kHz) using a piston pump at a flow rate of 1.5 ml/min, while feeding dry air at 180° C. to obtain microspheres. The formed microspheres were suspended in 0.5M lysine aqueous solution containing 1% (W/V) polyvinyl alcohol (Gohsenol, EG-50) as protective colloids, followed by stirring the same for 3 hours, recovering, washing with distilled water and lyophilising the microspheres to yield a formulation.

1.25 ml of a diluent (including 0.5% sodium carboxymethyl cellulose, 5.0% D-mannitol and 0.1% Tween 80 (pH 6.66)) was added to 125 mg of PT320 a powder state obtained through the above process to prepare a PT320 diluent. The prepared diluent was used and administered to experimental animal models.

Example 2. Confirmation of Effect of Inhibiting Levodopa-Induced Dyskinesia Progression In the present example, it was confirmed whether SR-exenatide (PT320) has effects of inhibiting the progression of levodopa induced dyskinesia.

Example 2-1. Administration Route and Dosage of SR-Exenatide (PT320) and L-DOPA The schedules of PT320 and L-DOPA drug treatment are shown in FIG. 1. Referring to the schedules, 6-OHDA was firstly injected into the right medial forebrain bundle at 0.25 μl/min for 10 minutes to induce lesions, and then treated with L-DOPA or L-DOPA+PT320 for 22 days, L-DOPA was dissolved in saline together with benserazide (15 mg/kg) and administered at 6 mg/kg/day by intraperitoneal injection (ip), PT320 (100 mg/kg, containing 2 mg/kg exenatide) was administered once a week (3 times in total) by subcutaneous injection (sc) hour before L-DOPA administration, so as to confirm the efficacy of inhibiting the progression of levodopa-induced dyskinesia according to drug treatment.

Example 2-2. Assessment of Abnormal Involuntary Movements (AIMs)

Figure 2:
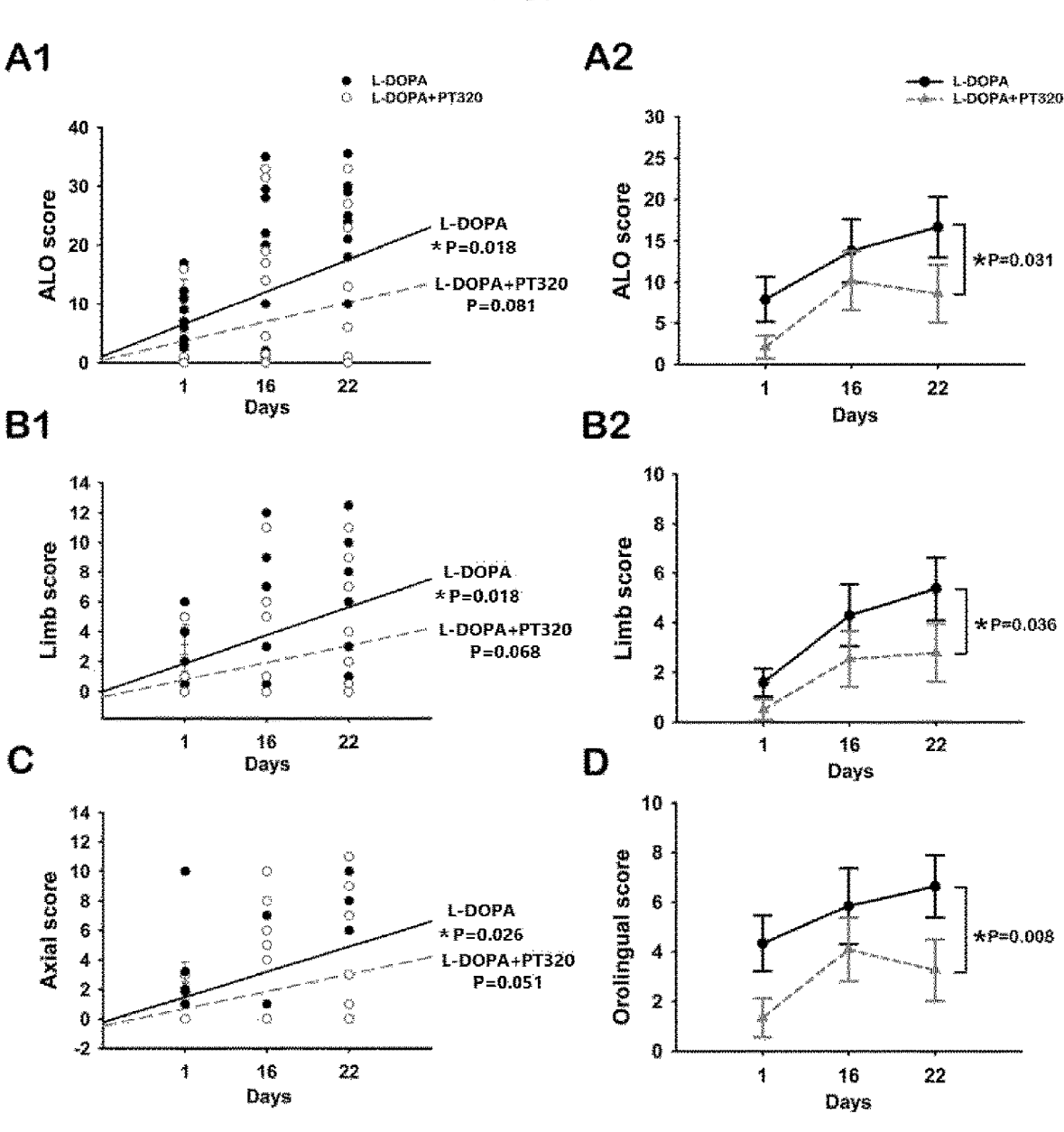
FIG. 2 is a graph confirming the effect of reducing AIMs by treatment with a controlled-release formulation (PT320) of the GLP-1 receptor agonist according to an example of the present invention in rats in which lesions were induced with 6-OHDA.

After placing all experimental animals in clear Perspex boxes (22 cm×34 cm×20 cm), each rat was observed for 1 minute at a 30 minute interval from 3 hours after L-DOPA administration (off-medication state) with regard to 4 types of items shown in Table 1 below. Each type was scored from 1 to 4 according to the criteria in Table 1 (1=appear less than 30 seconds; 2=appear 30 seconds or more; 3=appear throughout 1 minute but inhibited by external stimuli; 4=appear throughout 1 minute and not inhibited by external stimuli), and the observed results are shown in FIG. 2. At this time, ALO score means the sum of items 2 to 4, and animals with an ALO cumulative score lower than 10 were excluded from the assessment.

TABLE 1

| 4 types of items for assessment | |
|---|---|
| 1) Locomotion (Lo) & rotation | Increased locomotion contralateral to the lesion |
| 2) Limb (Li) | Random uncontrollable movements of forelimb contralateral to the lesion |
| 3) Orolingual (Ol) | Excess chewing and jaw movements with protrusion of the tongue |
| 4) Axial (Ax) | Dystonic postures or choreiform twisting of the neck and upper body towards the contralateral side |

4 Types of Assessment Items for AIMs

Referring to FIG. 2, when PT320 was treated in rats having lesions induced with 6-OHDA, all four behavioral scores were lower than those of a group treated with L-DOPA only. Accordingly, it was confirmed that the controlled-release formulation (PT320) of the GLP-1 receptor agonist according to an embodiment of the present invention is a composition to reduce ATMs.

Example 2-3. Measurement of Change in Dopamine

In the striatum, dopamine (DA), dopamine metabolites and dopamine turnover, which were changed by treatment with the controlled-release formulation (PT320) of the GLP-1 receptor agonist according to an example of the present invention, were measured by high-performance liquid chromatography (HPLC).

Using the brain of the rat whose behavioral evaluation was completed in Example 2-2, tissues of the lesion site and the lesion-free site were homogenized in 0.1N perchloric acid (HClO4). Thereafter, centrifugation was conducted at 13,000 rpm and at 4° C. for 30 minutes to collect a supernatant (50 μl), followed by diluting the same in perchloric acid (1:4, v/v) and injecting the diluted solution into HPLC. Tissue concentrations of DA and DA metabolites were analyzed by a coulometric detection system connected to HPLC. The HPLC mobile phase contained methanol (7%), monosodium phosphate (NaH2PO4, 70 mM), triethyiamine (100 μl/l), EDTA (0.1 mM) and sodium octylsulfate (100 mg/l) in deionized water, and was adjusted with orthophosphoric acid to reach pH 4.2 and used. The mobile phase was analyzed through an HPLC column (Hypersyl, C18, 15 cm×4.6 mm, particle size 5 μm) at a flow rats of 1.2 ml/min.

Figure 3:
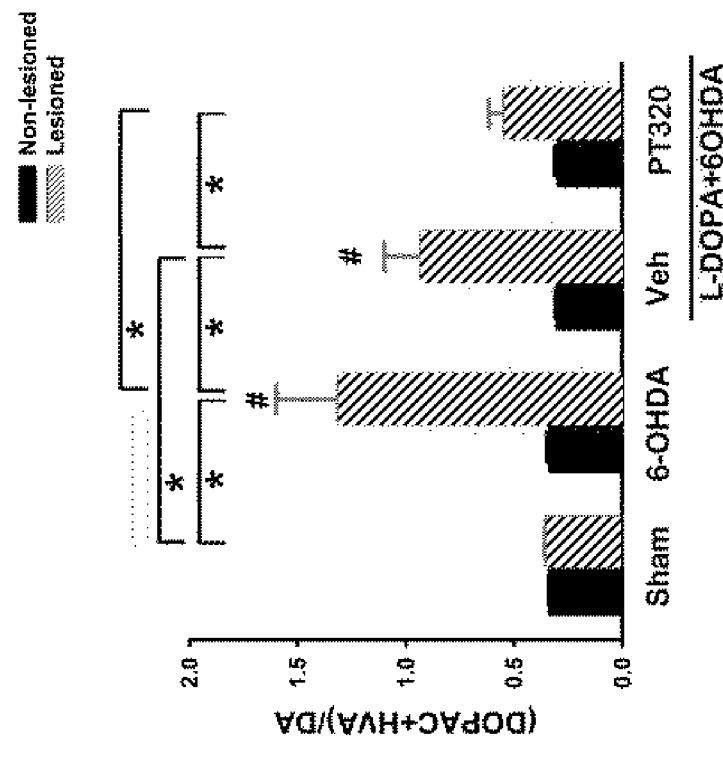
FIG. 3 is a graph confirming the turnover of dopamine (DA) normalized by treatment with a controlled-release formulation (PT320) of the GLP-1 receptor agonist according to an example of the present invention in the striatum.
Figure 3:
Figure 3:
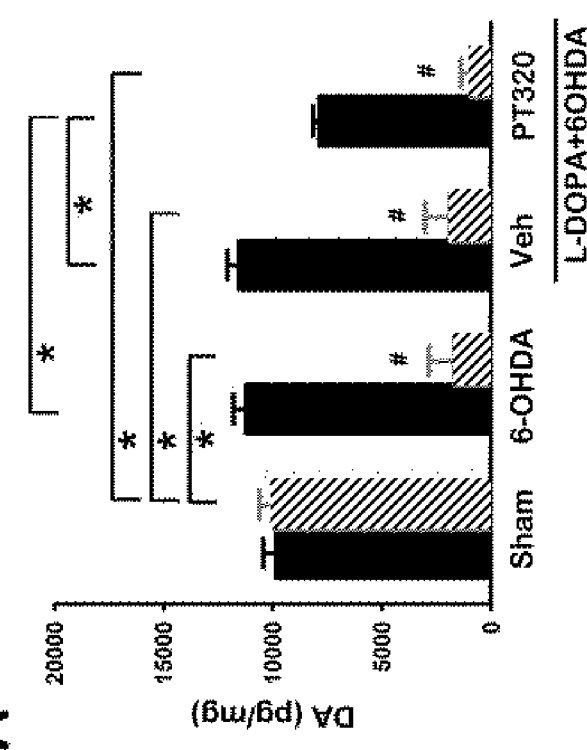

As shown in FIG. 3, when PT320 was used for treating rats in which lesions were induced with 6-OHDA, a DA turnover in the striatum was improved by 6-OHDA lesions, but was confirmed that the DA turnover for PT320 was normalized.

Example 3. Confirmation of Levodopa-Induced Dyskinesia Treatment Effect

In the present example, in order to confirm the efficacy of SR-exenatide (PT320) in treating levodopa-induced dyskinesia, abnormal involuntary movements (AIMs) were assessed.

Example 3-1. Construction of Animal Model

Experimental animal models for assessment of AIMs were constructed as follows, and all experimental animals were subjected to implement approved by IACUC and according to KFDA guidelines.

First, 6 to 7 weeks old SD rats (male, Koatech, Korea, Total N=30 (n=10 per group)) were acclimated to a typical light-dark cycle condition (7:00-20:00 hours) at a temperature of 22±1° C. and a humidity of 30 to 50%, Thereafter, Parkinson's disease was induced in SD rats, and 6-hydroxydopamine (2.5 μl at a concentration of 3 μg/μl dissolved in 0.1% ascorbic acid in sterile water) was injected alone in the medial forebrain bundle at 0.25 μl/min for 10 minutes using a Hamilton syringe after anesthesia.

After surgery (week 1 or 2), lesion-induced rats were subjected to an apomorphine hydrochloride-induced rotation test (0.5 mg/kg, i.p.), and all animals exhibiting systemic turnover ratio toward non-lesion area at least 7 times per minute (7 full body turn/min) were screened for the next experiments. Using the selected animals, a control group treated with 10 mg/kg L-DOPA (i.p.) and 15 mg/kg benserazide (i.p.) once a day, as well as PT320 experiment groups under the same conditions as the control group were constructed. In particular, in the case of the experimental group, PT320 was firstly administered, and then L-DOPA and benserazide were administered 1 hour later.

TABLE 2

| Division | Conditions |
|---|---|
| G1 (L-Dopacontrol) | 6OHDA lesion + L-DOPA (10 mpk; IP) @ WK 2 + vehicle |
| G2 (PT320 2 wk) | 6OHDA lesion + L-DOPA (10 mpk; IP) @ WK 2 + PT320 2 mpk @ WK 2 |

Administration Dosage and Condition Per Group

Example 3-2. Assessment of Abnormal Involuntary Movements (AIMs)

ATMs were assessed once a week after PT320 treatment till the 6th week of the experiment, at which the experiment is terminated. The assessment was performed in the same manner as in Example 2-2. The final AIMs calculation results according to this assessment method are shown in FIG. 4.

Figure 4:
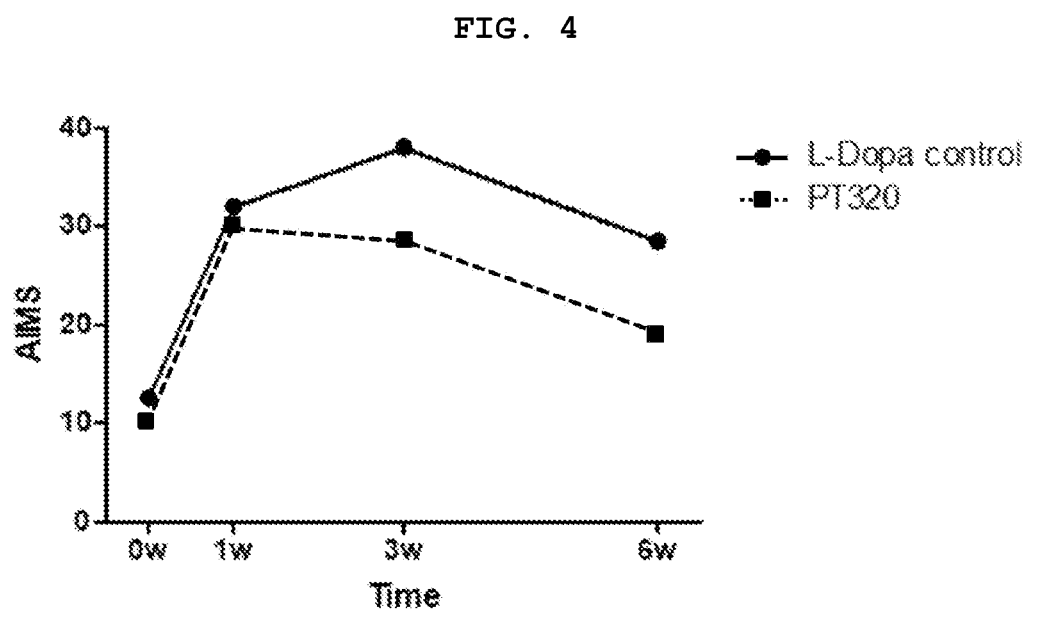

As can be seen in FIG. 4, according to the present experiment, it could be confirmed that SR-exenatide (PT320) exhibited treatment efficacy in a time-dependent manner in the experimental animal model in which levodopa-induced dyskinesia was induced.

What is claimed is:

1. A method for treatment of levodopa-induced dyskinesia, the method comprising:
    subcutaneously administering a composition comprising a therapeutically effective amount of a controlled-release formulation of an exendin-4 or exenatide to a patient with the levodopa-induced dyskinesia,
    wherein the controlled-release formulation comprises:
    a core containing the and a biodegradable polymer, wherein the biodegradable polymer comprises at least one selected from the group consisting of: polylactide, polyglycolide, and poly (lactide-co-glycolide) as a copolymer of lactide and glycolide; and
    a coating layer coated on the core,
    the coating layer comprising at least one selected from the group consisting of basic amino acid, polypeptide and an organic nitrogen compound,
    wherein the subcutaneous administration of the composition results in a reduction in abnormal involuntary movements (AIMs) as assessed by an AIMs scoring system.

2. The method according to claim 1, wherein the patient has received administration of levodopa.

3. The method according to claim 1, wherein the composition is administered after administration of levodopa.

4. The method according to claim 1, wherein the therapeutically effective amount ranges from 0.01 µg/kg/day to 100 µg/kg/day.

5. The method of claim 1, wherein the coating layer comprises one or more basic amino acids, wherein the basic amino acid comprises at least one selected from the group consisting of arginine, lysine and histidine.

6. The method according to claim 1, the intrinsic viscosity of the biodegradable polymer is 0.1 to 0.5 dl/g.

7. A method for prevention of levodopa-induced dyskinesia in a patient with a Parkinson's disease, the method comprising:

subcutaneously administering a composition comprising a prophylactically effective amount of a controlled-release formulation of an exendin-4 or exenatide to the patient who does not involve occurrence of levodopa-induced dyskinesia, wherein the patient has received administration of levodopa,

wherein the controlled-release formulation comprises:

a core containing the exendin-4 or the exenatide- and a biodegradable polymer, wherein the biodegradable polymer comprises at least one selected from the group consisting of: polylactide, polyglycolide, and poly (lactide-co-glycolide) as a copolymer of lactide and glycolide; and a coating layer coated on the core, the coating layer comprising at least one selected from the group consisting of basic amino acid, polypeptide and an organic nitrogen compound, wherein the subcutaneous administration of the composition results in a reduction in abnormal involuntary movements (AIMs) as assessed by an AIMs scoring system.

8. The method of claim 7, wherein the composition is administered simultaneously with levodopa or after administration of levodopa.

9. The method of claim 7, wherein the prophylactically effective amount ranges from 0.01 µg/kg/day to 100 µg/kg/day.

10. The method according to claim 7, the intrinsic viscosity of the biodegradable polymer is 0.1 to 0.5 dl/g.

* * * * *